May 4, 1965 H. KERRIGAN Plant Pat. 2,505
AZALEA PLANT
Filed Dec. 27, 1963
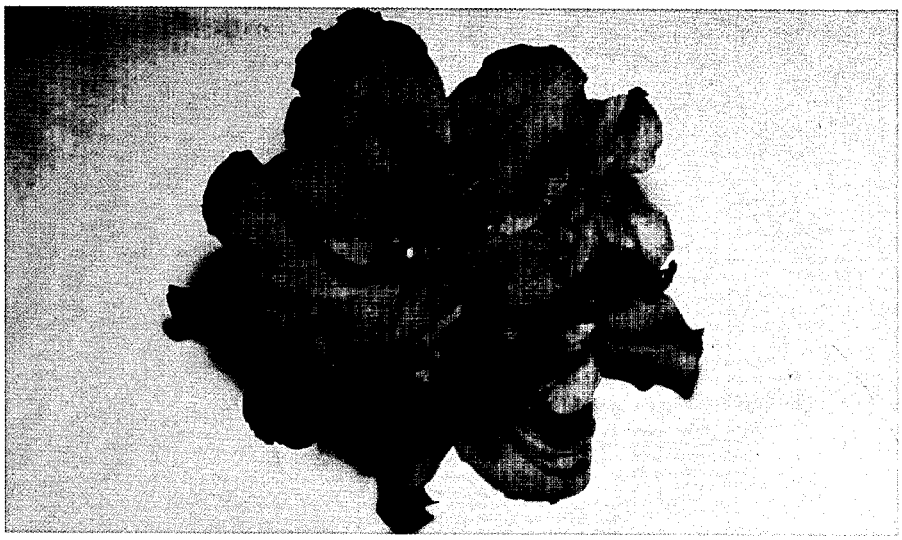
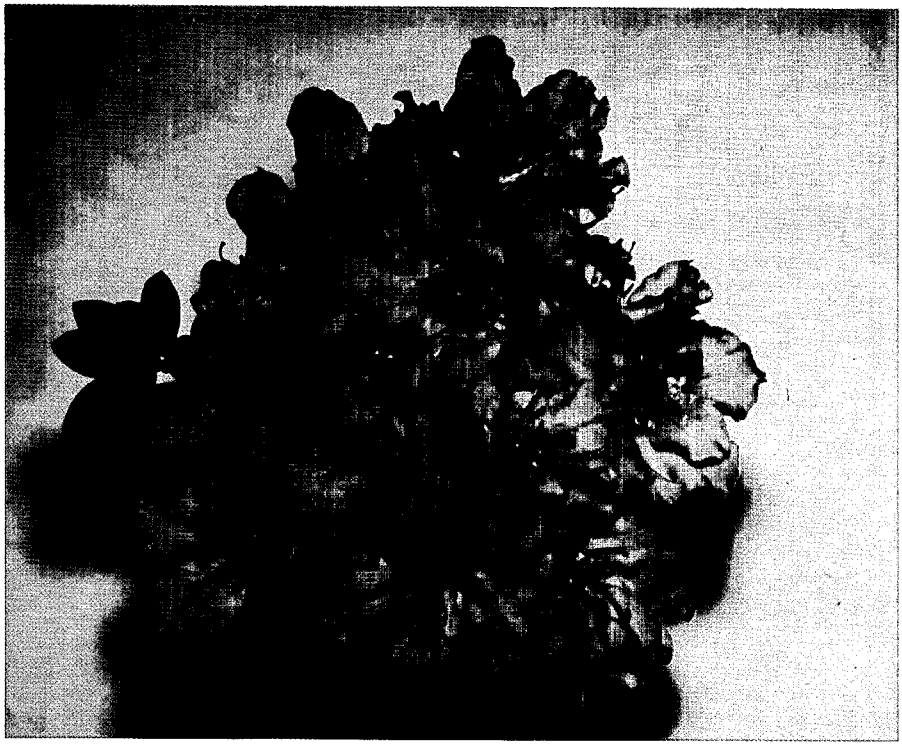

United States Patent Office

Plant Pat. 2,505
Patented May 4, 1965

2,505
AZALEA PLANT

Howard Kerrigan, 3003 Totterdell St., Oakland, Calif.

Filed Dec. 27, 1963, Ser. No. 334,062
1 Claim. (Cl. Plt.—57)

This disclosure concerns a new and distinct variety of azalea plant of the large flowered forcing type closely resembling the typical Belgian Indica varieties. This variety of azalea was developed by me at Oakland, California, in 1952, as a result of a breeding program begun in 1943.

The main objective of this particular phase of said breeding effort was the production of a variety of azalea of the Belgian Indica type which bore flowers of a clear Blood Red color and of large size on a compact plant which would set buds as heavily as the variety "Miss Cottage Gardens" and to combine these characteristics in a plant of greater vigor bearing flowers of a clearer, richer red color than the variety "Miss Cottage Gardens."

This objective was achieved in this variety which is a hand pollinated seedling obtained by crossing the variety, L. C. Bobbink (Plant Patent 611, expired), the seed parent with the variety, Miss Cottage Gardens (not patented), the pollen parent.

In addition to the desired improvements heretofore unknown in azaleas of this type several other unique and distinguishing characteristics exist. The retention of the flowers on the plant when forced is significantly better than the seed parent, the color is more stable and is of a true Blood Red hue. The flowers never blues when forced as does the seed parent and the growth of the plant is superior. The flower form and color are conspicuously better than those of the pollen parent. The plant habit is similar to the pollen parent but the rate of growth is much greater and the color and polish of the foliage is superior to that of the pollen parent. My new variety most closely resembles the variety "Miss Cottage Gardens" in profusion of bloom, heavy bud set, and compact habit.

These characteristics have all proven consistent and stable during the course of successive asexual generations of plants propagated by me at Oakland, California, since 1954 from soft wood cuttings.

The following are detailed horticultural and botanical descriptions of my new variety of azalea plant. The color designations are those employed in the Horticultural Colour Chart issued by Wilson Colour Ltd. in collaboration with the Royal Horticultural Society.

*Horticultural description*

Semi-evergreen shrub of unusually rapid growth for an azalea of the Belgian Indica type, densely and profusely branched even without extensive pruning or pinching. The internodes are short, resulting in little or no coarse growth. The mature form is a densely branched spreading shrub 12"–18" tall and spreading to 20"–24" wide. The stems are slender, covered with a dense layer of dark brown hairs. The leaves are very shiny, dark green, medium sized and extremely abundant. The color of the upper leaf surface is Ivy Green (HCC ooo1060/3). The lower surface is Spinach Green (HCC o960/3). The lower surface often appears somewhat red-brown due to a dense pubescence along the veins and a moderate pubescence of the intervenal areas.

The flowers are borne in clusters of 2–4.

The calyx is normal, five, sometimes six lobed, Spinach Green. Sepals less than ¼ inch long and half as broad as long, densely pubescent, margins entire.

The corolla is large and showy, broadly flaring with five to six lobes, 1⅜ inches deep and 3⅛ inches across.

The petal lobes are large and wavy edged. The flower color is Blood Red (HCC 820/3) and the color is maintained throughout the life of the flower. The upper portion of the throat of the flower and the lower portion of the upper three lobes are marked conspicuously with Chrysanthemum Crimson (HCC 824/1) blotches which in some flowers extend to the base of the throat.

The stamens are modified into large petaloids for the most part though in many flowers an occasional perfect stamen can be found. Another tissue is often present on the smaller innermost petaloids. The petaloids themselves are Blood Red, 8–10 in number, pleated and ruffled and extremely variable in size, ordinarily fused at their bases into a short tube and 1⅛ inches to ⅝ inch long exclusive of the tube.

The pistil is 1⅞ inches long. The stigma is Chrysanthemum Crimson, triangular. The style is 1⅝ inches long, curved, and extending somewhat beyond the petaloids. The tip of the style curves sharply upward.

The ovary is obscured by very dense white hairs that extend well up the style.

The blooming habit is extremely profuse and the variety when properly handled can be forced at virtually any time. It can be induced to set buds with remarkable ease very early in the season.

*Botanical description*

Semi-evergreen, low, spreading shrub to 18" tall and 24" wide. The young shoots slender, densely strigose; pubescence dark brown with hyaline margins, long lanceolate, pointed, entire. The length of the hairs is variable, exhibiting essentially two classes, one long and conspicuous, the other, small, short and stout to fine. The older shoots are brown, striated. The internodes are short. The branching habit is dense and compact.

The foliage is oblanceolate 1½ inches long by 9/16 inch wide, petiolate, the petiole ¼ inch long, strigose; the hairs 3/32 inch long, lanceolate, dark brown with entire hyaline margins. The blade dark green above, nitid, glabrous; venation conspicuous pale green. The lower surface of the leaf light green, the mid-vein very prominent densely pubescent, the hairs dark brown. The leaf margin is entire, ciliate. The leaf apex is mucronate. The young foliage is light green and densely pubescent above and below.

The inflorescence bears 2–4 flowers on short pedicels about ⅜ inch long. The pedicels are red-brown densely pubescent. The pubescence is white to straw colored.

The calyx is normal 5–6 lobed. The sepals are triangular twice as long as broad, about 3/16 inch long, entire, densely pubescent.

The corolla is broadly uniform five to six lobed with a short flaring tube. The corolla is nearly three times as broad as deep. A typical specimen measures 3⅛ inches across and 1⅜ inches deep. The corolla limbs are large, strongly auriculate 1⅜ inches long by 1¼ inches wide. The margins of the limbs are undulate, entire. The corolla is Blood Red except for conspicuous deep crimson markings on the dorsal portion of the tube and on the proximal portion of the three dorsal limbs.

The stamens are modified into petaloids for the most part. An occasional perfect stamen is sometimes found but these are rare. The petaloids are Blood Red except that the dorsal ones may have considerable deep crimson markings like those of the corolla. The petaloids number from 8–10. They are ordinarily fused at their bases into a short tube. The tube is ⅝ inch long, narrowly flaring. The free portion of the petaloids varies from ⅝ inch to 1⅛ inches long. The tube is grooved and pleated.

The pistil is 1⅞ inches long. The stigma is exserted, triangular deep crimson, and oriented in a horizontal plane. The style is Blood Red, 1⅝ inches long, slender, sigmoid with the distal portion abruptly ascending. The ovary is densely setose. The pubescence is white, hyaline, exceeding the ovary by nearly its length and completely obscuring the ovary.

Having disclosed my invention in the above descriptions and in the accompanying drawings which are as accurately representative of the natural colors as available methods will permit and which substantially illustrate the distinctive characteristics of my variety which may be disclosed by these means what I claim is new and patentable is:

A new and distinct variety of florists' forcing azalea similar in general character to the Belgian Indica type, primarily characterized by its deep Blood Red color, large double flowers of the classical form which are borne in unusual profusion and which are retained on the flower for a long period in an essentially fresh condition, by its significantly greater vigor and more rapid growth than other varieties of red colored forcing azaleas.

No references cited.

ABRAHAM G. STONE, *Primary Examiner.*